US010789266B2

(12) United States Patent
Bhabesh et al.

(10) Patent No.: US 10,789,266 B2
(45) Date of Patent: Sep. 29, 2020

(54) SYSTEM AND METHOD FOR EXTRACTION AND CONVERSION OF ELECTRONIC HEALTH INFORMATION FOR TRAINING A COMPUTERIZED DATA MODEL FOR ALGORITHMIC DETECTION OF NON-LINEARITY IN A DATA

(71) Applicant: INNOVACCER INC., San Francisco, CA (US)

(72) Inventors: Gourav Sanjukta Bhabesh, Baripada (IN); Vibhuti Agrawal, Delhi (IN)

(73) Assignee: INNOVACCER INC., San Francisco, CA (US)

( * ) Notice: Subject to any disclaimer, the term of this patent is extended or adjusted under 35 U.S.C. 154(b) by 0 days.

(21) Appl. No.: 16/363,897

(22) Filed: Mar. 25, 2019

(65) Prior Publication Data
US 2020/0257697 A1 Aug. 13, 2020

(30) Foreign Application Priority Data
Feb. 8, 2019 (IN) .............................. 201921005031

(51) Int. Cl.
*G06N 20/20* (2019.01)
*G06N 5/04* (2006.01)
(Continued)

(52) U.S. Cl.
CPC ........ *G06F 16/258* (2019.01); *G06F 16/1824* (2019.01); *G06N 5/04* (2013.01);
(Continued)

(58) Field of Classification Search
CPC ... G06F 16/258; G06F 16/1824; G16H 50/20; G06N 20/20; G06N 20/10; G06N 5/04
See application file for complete search history.

(56) References Cited

U.S. PATENT DOCUMENTS 6,408,294 B1 6/2002 Getchius ........... G06F 16/24534
6,484,161 B1 11/2002 Chipalkatti ............ G06Q 30/02
(Continued)

FOREIGN PATENT DOCUMENTS

WO WO 2018/057647 3/2018 ............... C12Q 1/68
WO WO 2018/166853 9/2018 ............. G16H 10/60

OTHER PUBLICATIONS

Mohammad Amin Morid, Supervised Learning Methods for Predicting Healthcare Costs: Systematic Literature Review and Empirical Evaluation, 2018, AMIA Annu Symp Proc. pp. 1312-1321 (Year: 2018).*

(Continued)

*Primary Examiner* — Eric Nilsson
*Assistant Examiner* — Ahsif A. Sheikh
(74) *Attorney, Agent, or Firm* — Hayes Soloway P.C.

(57) ABSTRACT

A system and method for training a computerized data model for the algorithmic detection of non-linearity in a data set includes providing two master data sets corresponding to two discrete time periods, respectively, and a third data set for a third discrete time period. The two master data sets are mapped to at least one code model. A stacking average model is trained with the at least two master data sets corresponding to two discrete time periods by using a stacked regression algorithm. A box-cox transformation function is applied to the models to provide a predicted value for the third data set of the third discrete time period. An ensemble is created using the predicted value for the third data set and the first, second, and third models of the trained stacking average model to identify a non-linearity in the third data set.

22 Claims, 8 Drawing Sheets

(51) Int. Cl.
*G06N 20/10* (2019.01)
*G16H 50/20* (2018.01)
*G06F 16/25* (2019.01)
*G06F 16/182* (2019.01)

(52) U.S. Cl.
CPC ............ *G06N 20/10* (2019.01); *G06N 20/20* (2019.01); *G16H 50/20* (2018.01)

(56) References Cited

U.S. PATENT DOCUMENTS

| | | | |
|---|---|---|---|
| 7,047,242 B1 | 5/2006 | Ponte | G06Q 10/00 |
| 7,611,466 B2 | 11/2009 | Chalana | A61B 8/0858 |
| 8,849,693 B1 | 9/2014 | Koyfman | G06Q 30/02 |
| 8,977,953 B1 | 3/2015 | Pierre | G06F 40/284 |
| 9,542,393 B2 | 1/2017 | Morton | G06F 16/7844 |
| 9,727,591 B1 | 8/2017 | Sharma | G06F 16/215 |
| 10,056,078 B1 | 8/2018 | Shepherd | G06F 16/632 |
| 10,147,504 B1* | 12/2018 | Stettin | G16H 50/30 |
| 2003/0018633 A1* | 1/2003 | Horn | G06F 17/18 |
| 2004/0215629 A1 | 10/2004 | Dettinger | G06F 16/2452 |
| 2005/0065956 A1 | 3/2005 | Brown | G06F 16/252 |
| 2005/0107902 A1 | 5/2005 | Blouin | G06Q 10/087 |
| 2005/0119534 A1 | 6/2005 | Trost | G06F 19/00 |
| 2005/0131778 A1 | 6/2005 | Bennett | G06Q 10/0875 |
| 2006/0041539 A1 | 2/2006 | Matchett | G06Q 10/0639 |
| 2006/0075001 A1 | 4/2006 | Canning | G06F 8/65 |
| 2007/0239724 A1 | 10/2007 | Ramer | G06F 16/951 |
| 2009/0313232 A1 | 12/2009 | Tinsley | G06Q 30/02 |
| 2010/0121879 A1 | 5/2010 | Greenberg | G06F 16/248 |
| 2010/0199169 A1 | 8/2010 | Gnech | G06F 16/972 |
| 2010/0287162 A1 | 11/2010 | Shirwadkar | G06F 16/3338 |
| 2012/0253793 A1 | 10/2012 | Ghannam | G06F 17/27 |
| 2013/0197936 A1* | 8/2013 | Willich | G06Q 50/22 705/3 |
| 2014/0006061 A1 | 1/2014 | Watanabe | G06Q 30/02 |
| 2014/0149446 A1 | 5/2014 | Kuchmann-Beauger | G06F 17/30389 |
| 2014/0188835 A1 | 7/2014 | Zhang | G06F 17/2705 |
| 2014/0344261 A1 | 11/2014 | Navta | G06F 16/951 |
| 2015/0164430 A1 | 6/2015 | Hu | A61B 5/7264 |
| 2015/0363478 A1 | 12/2015 | Haynes | G06F 16/26 |
| 2016/0098387 A1 | 4/2016 | Bruno | G06F 17/27 |
| 2016/0162473 A1 | 6/2016 | Cogley | G06F 40/51 |
| 2016/0371453 A1 | 12/2016 | Bowman | G06F 19/00 |
| 2016/0373456 A1 | 12/2016 | Vermeulen | G06F 16/25 |
| 2017/0091162 A1 | 3/2017 | Emanuel | G06F 40/169 |
| 2017/0102693 A1 | 4/2017 | Kidd | G05B 19/41865 |
| 2017/0161372 A1 | 6/2017 | Fernandez | G06F 16/35 |
| 2017/0199928 A1 | 7/2017 | Zhao | G06F 16/24578 |
| 2017/0256173 A1 | 9/2017 | Burford | G09B 5/125 |
| 2017/0344646 A1 | 11/2017 | Antonopoulos | H04L 9/008 |
| 2017/0371881 A1 | 12/2017 | Reynolds | G06F 16/248 |
| 2018/0052842 A1 | 2/2018 | Hewavitharana et al. | G06F 17/3043 |
| 2018/0158146 A1 | 6/2018 | Turner | G06Q 40/02 |
| 2018/0225320 A1* | 8/2018 | Saini | G06F 16/215 |
| 2018/0232443 A1 | 8/2018 | Delgo | G06Q 30/06 |
| 2018/0367557 A1 | 12/2018 | Brown | H04L 63/1425 |
| 2019/0012390 A1 | 1/2019 | Nishant | G06N 20/00 |
| 2019/0050445 A1 | 2/2019 | Griffith | G06K 9/6262 |
| 2019/0156198 A1 | 5/2019 | Mars | G06N 20/20 |
| 2019/0179820 A1 | 6/2019 | El Kaed | G06F 16/2471 |
| 2019/0180757 A1 | 6/2019 | Kothari | G10L 17/005 |
| 2019/0324964 A1 | 10/2019 | Shiran | G06N 20/00 |
| 2020/0004749 A1 | 1/2020 | Slezak | G06F 16/2462 |

OTHER PUBLICATIONS

Mohammad Amin Morid, Supervised Learning Methods for Predicting Healthcare Costs: Systematic Literature Review and Empirical Evaluation, 2018, AMIA Annu Symp Proc. pp. 1312-1321 (Year: 2018).*

B. Wang, Y. Wang, K. Qin and Q. Xia, "Detecting Transportation Modes Based on LightGBM Classifier from GPS Trajectory Data," 2018 26th International Conference on Geoinformatics, Kunming, 2018, pp. 1-7. (Year: 2018).*

Lufa Zhang, Nan Liu, Health reform and out-of-pocket payments: lessons from China, Health Policy and Planning, vol. 29, Issue 2, Mar. 2014, pp. 217-226, https://doi.org/10.1093/heapol/czt006 (Year: 2014).*

A. Iyengar, A. Kundu, U. Sharma and P. Zhang, "A Trusted Healthcare Data Analytics Cloud Platform," 2018 IEEE 38th International Conference on Distributed Computing Systems (ICDCS), Vienna, 2018, pp. 1238-1249. (Year: 2018).*

Office Action issued in U.S. Appl. No. 16/387,016, dated Jun. 25, 2019 (11 pgs).

Office Action issued in U.S. Appl. No. 16/387,016, dated Oct. 17, 2019 (17 pgs).

Notice of Allowance issued in U.S. Appl. No. 16/387,016 dated Feb. 10, 2020 (15 pgs).

Office Action issued in U.S. Appl. No. 16/743,175 dated Mar. 23, 2020 (21 pgs).

International Search Report and Written Opinion issued in PCT/US20/13802 dated Mar. 25, 2020 (10 pgs).

International Search Report and Written Opinion issued in PCT/US20/16827 dated Apr. 22, 2020 (7 pgs).

* cited by examiner

SYSTEM AND METHOD FOR EXTRACTION AND CONVERSION OF ELECTRONIC HEALTH INFORMATION FOR TRAINING A COMPUTERIZED DATA MODEL FOR ALGORITHMIC DETECTION OF NON-LINEARITY IN A DATA

CROSS REFERENCE TO RELATED APPLICATION

This application claims benefit of Indian Application Serial No. 201921005031 filed Feb. 8, 2019, the entire disclosure of which is incorporated herein by reference.

FIELD OF THE DISCLOSURE

The present disclosure is generally related to computerized data modeling and more particularly is related to a system and method of extraction and conversion of electronic health information for training a computerized data model for algorithmic detection of non-linearity in a data set.

BACKGROUND OF THE DISCLOSURE

In modern society, computer modeling techniques are used with increasing frequency to analyze large data sets in order to extract valuable data points. These data points can frequently be used to improve efficiency, decrease costs, and improve performance in an industry from which the large data set is derived. As more and more sectors and industries implement computerized record keeping, it becomes possible to further analyze the data within these records to improve aspects of the industry, which in turn, can be used to improve the lives of individual human beings.

Within the healthcare field in particular, predicting the health cost of patients with higher accuracy is desired by many health care providers, insurers, and other health care entities as it enables them to take preventive steps with more confidence in managing the health status of patients. With the digitization of health data there has been a race to use this huge data to better manage the lives of the patients and empower the health organizations to become more preventive in actions. The health data has been very difficult to quantify as the same disease can have very different complications in one patient compared to another, which can arise either due to the interaction of one prior disease with the onset of another or the poor quality of care given to the patient leading to some other complications. All these non-quantifiable parameters lead to a non-linear trend of the cost incurred by the patients.

Researchers have tried earlier to make parsimonious models using the demographics information to predict the health cost of various populations but have achieved very low accuracy. The main reason for this is the non-linear trend in the data, one patient in the test set with very similar pattern of demographics as in the training set can have very different costs in the coming years and the cause for it are multiple. Then other models have tried using the claims data to predict the cost which captures the disease burden of the patients but fails to take into account the demographics; as one place can have a very different lifestyle leading to an increase in a particular form of disease say diabetes compared to another, where people follow a more healthy lifestyle. There have been models which have tried to take the demographics and the claims data together and have shown good accuracy but then it fails to capture the more episodic events such as operations or readmissions or laboratory tests which all cause a significant health cost.

Another serious problem with the cost health data is the non-linear format leading to failure of many simple regression models such as simple linear regression. Thus getting a complete picture of the medical history of a patient and quantifying it to meaningful numbers for the algorithms to work on is a major challenge. Moreover, because of this challenge, it is difficult to use computerized models to aid in assessment of the data. Computerized models need to utilize algorithms that can understand the underlying non-linearity in the data that can give a solid model to predict the future health care data, such as cost of treatment of the patients, such that a treatment path for the patient can be adjusted to optimize their care relative to the cost of their care.

Thus, a heretofore unaddressed need exists in the industry to address the aforementioned deficiencies and inadequacies.

SUMMARY OF THE DISCLOSURE

Embodiments of the present disclosure provide a method for training a computerized data model for the algorithmic detection of non-linearity in an electronic health information data set. In this regard, one embodiment of such a method, among others, can be broadly summarized by the following steps: providing at least two master data sets corresponding to two discrete time periods, respectively, and a third data set for a third discrete time period, wherein the two master data sets are mapped to at least one code model by at least one of: converting a quantity of electronic health information data in unstructured format to tabular format for storage on a hadoop distributed file system (HDFS); semantic unification of the quantity of electronic health information data; and mapping at least one diagnostic code within the quantity of electronic health information data to a hierarchical condition category (HCC) value using a HCC model, summing a plurality of HCC values, and processing the summed plurality of HCC values through a severity index. Training a stacking average model with the at least two master data sets corresponding to two discrete time periods by: using a first model comprising: a Kernel Ridge Regression (KRR) algorithm, an Elastic Net (ENet) algorithm, a Lasso algorithm, and a Gradient algorithm stacked together; using a second model comprising a Light Gradient Boosting (lgbm) algorithm; and using a third model comprising an Xtreme Gradient Boosting (xgboost) algorithm. Applying a box-cox transformation function to the first, second, and third models of the stacking average model to provide a predicted value for the third data set of the third discrete time period. Creating an ensemble using the predicted value for the third data set and the first, second, and third models of the trained stacking average model to identify a non-linearity in the third data set.

The present disclosure can also be viewed as providing methods for extraction and conversion of electronic health information data for algorithmic detection of non-linearity to determine treatment path. In this regard, one embodiment of such a method, among others, can be broadly summarized by the following steps: extracting, via a file transfer connection, a quantity of electronic health information data from a health database to a data lake on a computerized cloud server; mapping at least a portion of the quantity of electronic health information data to at least one code model to produce an initial data set; scripting the initial data set for preprocessing to determine a skewness of the initial data set, wherein the skewness of the initial data set is removed to provide master data associated with at least two discrete time periods; modeling the master data set for the at least two discrete time periods with a stacked regression model and a polynomial regression model to produce a predictive data set; transmitting the predictive data set to a data exchange platform, wherein the predictive data set provides a prioritization assessment of patients associated with the quantity of electronic health information data; and implementing the prioritization assessment in a care coordination facility to determine a treatment path of the patients, whereby the treatment path of at least one patient is adjusted.

The present disclosure can also be viewed as providing a system for computerized extraction and conversion of electronic health information data for algorithmic detection of non-linearity to determine treatment path. Briefly described, in architecture, one embodiment of the system, among others, can be implemented as follows. A quantity of electronic health information data is stored on a health database, wherein at least a portion of the quantity of electronic health information data is extracted via a file transfer connection to a data lake on a computerized cloud server. At least one code model is used to produce an initial data set, wherein the initial data set is produced by mapping at least a portion of the quantity of electronic health information data to the at least one code model. A script is used for scripting the initial data set for preprocessing to determine a skewness of the initial data set, wherein the skewness of the initial data set is removed to provide master data associated with at least two discrete time periods. A modeling engine is used to model the master data set for the at least two discrete time periods with a stacked regression model and a polynomial regression model to produce a predictive data set. The predictive data set is transmitted to a data exchange platform, wherein the predictive data set provides a prioritization assessment of patients associated with the quantity of electronic health information data. The prioritization assessment is transmitted to a care coordination facility, wherein the prioritization is implemented to determine a treatment path of the patients, whereby the treatment path of at least one patient is adjusted.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

The present disclosure is directed to training a computerized data model for algorithmic detection of non-linearity in a data set, and in particular, for computerized model analysis and prediction within the health care field. As discussed in detail herein, the computerized model analysis receives data inputs relating to a patient, such as a patient's demographics, claims and clinical historical data to predict the health cost that may be incurred in the subsequent years to come using the stacked regression algorithms. Particularly, the computerized modeling techniques may extract relevant data from the patient's medical history and quantify it in a particular format to prepare it for the stacked regression algorithm to predict the future cost of health for each patient. The models and algorithms used may also take into account the outliers, episodic jumps in the data and understands the hidden non-linearity pattern in the data for which stacked regression algorithm has proven to be useful and accurate.

Figure 1:
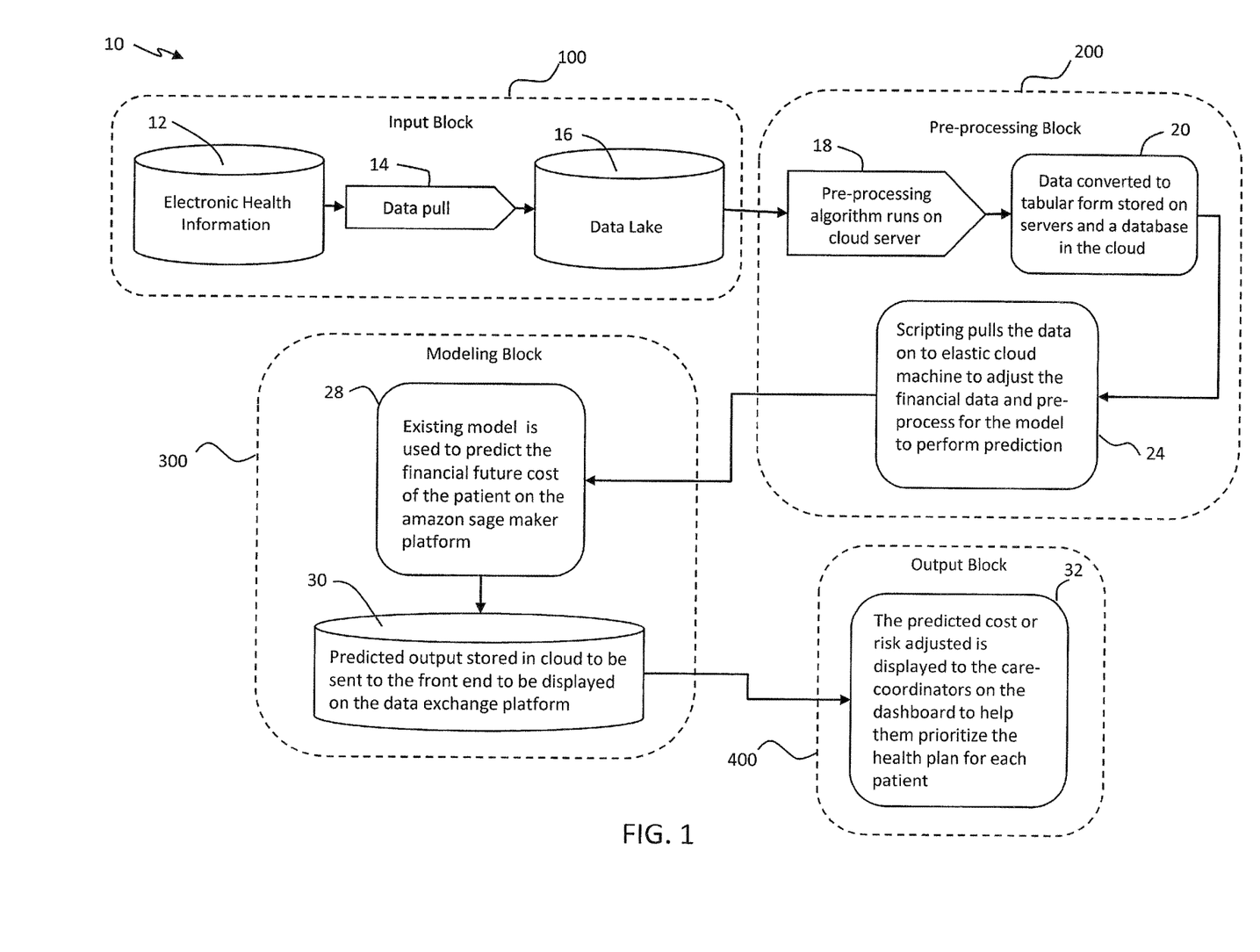
FIG. 1 is a diagrammatical illustration of a method of extraction and conversion of electronic health information data for training a computerized data model for algorithmic detection of non-linearity in a data set, in accordance with a first exemplary embodiment of the present disclosure.
Figure 2:
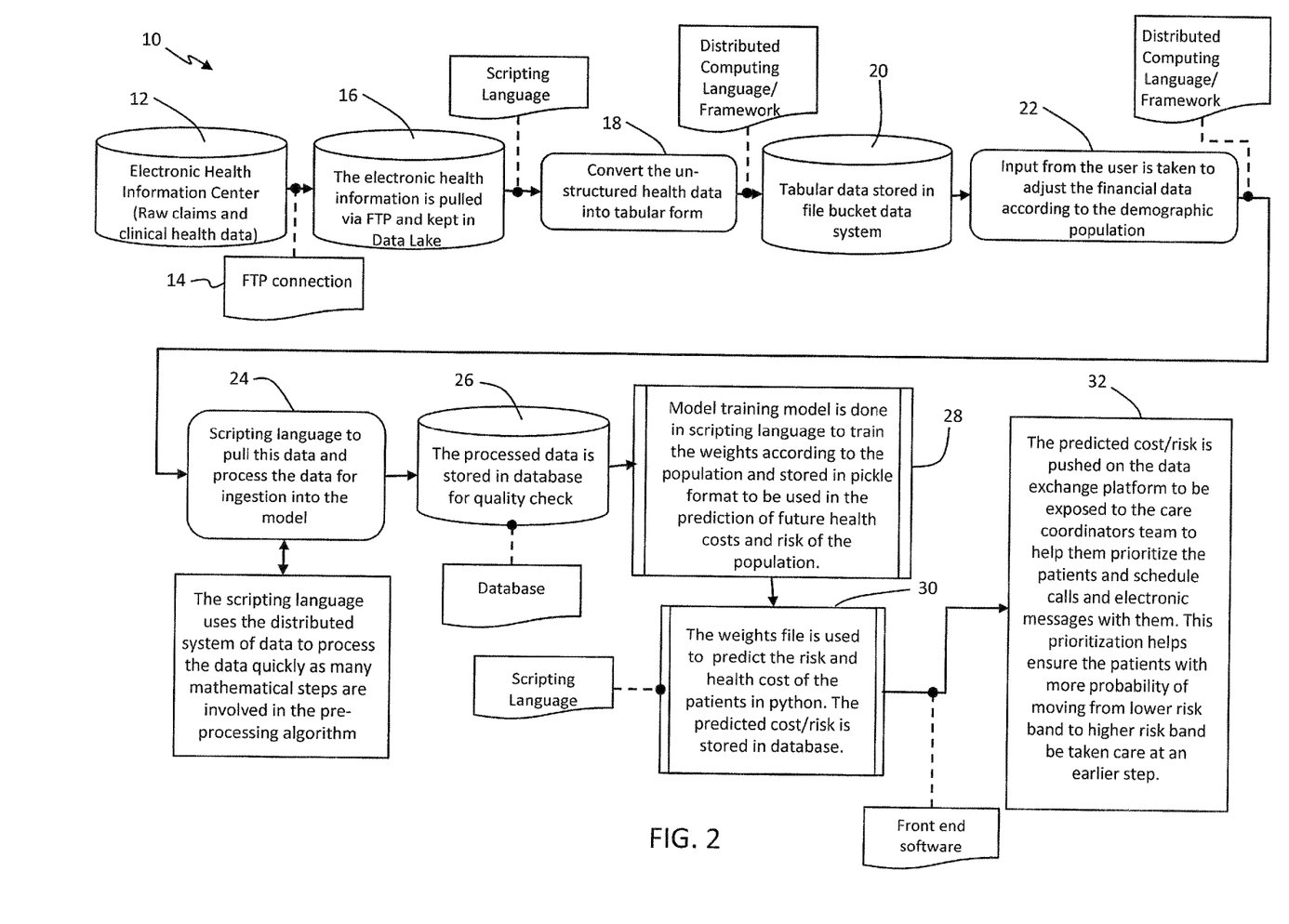
FIG. 2 is a detailed diagrammatical illustration of the method of extraction and conversion of electronic health information data for training a computerized data model for algorithmic detection of non-linearity in a data set of FIG. 1, in accordance with the first exemplary embodiment of the present disclosure.

FIG. 1 is a diagrammatical illustration of a method of extraction and conversion of electronic health information data for training a computerized data model for algorithmic detection of non-linearity in a data set 10, in accordance with a first exemplary embodiment of the present disclosure. FIG. 2 is a detailed diagrammatical illustration of the method of extraction and conversion of electronic health information data for training a computerized data model for algorithmic detection of non-linearity in a data set 10 of FIG. 1, in accordance with the first exemplary embodiment of the present disclosure. The method of extraction and conversion of electronic health information data for training a computerized data model for algorithmic detection of non-linearity in a data set 10 of FIGS. 1-2, which may be referred to herein as method 10, may generally include different blocks, including a data input block 100, a pre-processing block 200, a modeling block 300, and an output block 400, each of which is identified in FIG. 1. FIG. 2 provides a detailed explanation for each of the processing blocks along with exemplary computing functions which may be used therein.

The method for extraction and conversion of electronic health information data for algorithmic detection of non-linearity to determine treatment path may include various steps and functions, as disclosed herein. In one example, the method includes extracting, via a file transfer connection, a quantity of electronic health information data from a health database to a data lake on a computerized cloud server. At least a portion of the quantity of electronic health information data is mapped to at least one code model to produce an initial data set. The initial data set is scripted for preprocessing to determine a skewness of the initial data set, wherein the skewness of the initial data set is removed to provide master data associated with at least two discrete time periods. The master data set for the at least two discrete time periods is modeled with a stacked regression model and a polynomial regression model to produce a predictive data set. The predictive data set is then transmitted to a data exchange platform, wherein the predictive data set provides a prioritization assessment of patients associated with the quantity of electronic health information data. The prioritization assessment is then implemented in a care coordination facility to determine a treatment path of the patients, whereby the treatment path of at least one patient is adjusted.

The method is described further with reference to FIGS. 1-2. As shown, the input block 100 may generally be used to extract input data into the method 10. An electronic health information database 12, also known as a health electronic record database, may contain a variety of health care related information in raw form. For example, the electronic health information database 12 may include electronic medical record (EMR) data, other clinical data, claims data, or any other health-related data, all of which may be collectively refereed herein as electronic health information. The electronic health information database 12 may include a plurality of separate or interface databases located at each individual health care provider site, such as medical offices, hospitals, or other treatment facilities, or centrally located, such as within a centralized storage device. The electronic health information database 12 may include any type of raw medical data, such as medical claims data and clinical health data, among others, which has not been structured into a homogenous data set. The data may be classified or organized by individual patients or by groups of individuals, such as classes or demographics in individuals.

At least a portion of electronic health information data is extracted or pulled from the electronic health information database 12 to a data lake 16 on a computerized cloud server via Secure File Transfer Protocol (SFTP) connection 14. The data lake 16 is a repository of data which is stored in its natural format, commonly as object blobs or files. The data lake may be a single storage unit of all enterprise data including raw copies of source system data and transformed data used for tasks like analysis, modeling, or others, such as reporting, visualization, analytics, and machine learning. Because all of the electronic health information data within the electronic health information database 12 comes from various sources, a significant amount of standardizations often takes place. These standardizations may include refining the raw or unstructured electronic health information data to identify similar data points in common or structured ways, such that inconsistencies in the electronic health information data can be removed by converting the electronic health information data into a universal format. This may be referred to as semantic unification of the electronic health information data. As a simplistic example, dates associated with the electronic health information data should be standardized into a universal format. In another example, male and female patients may be coded differently for the same medical conditions. At block 18, the electronic health information data within the data lake 16 may then be converted to tabular form, such that the unstructured electronic health information data can be converted into an organized tabular format.

It is noted that the quality of the electronic health information data is also analyzed and cleaned to remove the unwanted data. In doing so, the specific health care domain is considered. For example, the test HBA1C, which measures sugar in a patient's blood, is common for diverticulitis patients. Typically, the test outputs ranges of values and oftentimes a decimal point or the unit of measurement is either forgotten or incorrectly input. This can occur when an administrator is inputting the values with a drop-down menu, where the administrator inadvertently selects the wrong data value. Cleaning of the data may filter out the unwanted data by identifying the inconsistency of the data value for the test and omitting it from the modeling.

Next, within the pre-processing block 200, various pre-processing algorithms may be run on a cloud server. In particular, at block 20, the tabular data may be stored in a cloud or on-premises storage service or file bucket, such as a hadoop distributed file system (HDFS) on a cloud server or another data store as may be used in the industry, however, the HDFS may be preferred as it is a distributed file-system which is capable of storing data on commodity machines, such that it can provide very high aggregate bandwidth across the cluster. At block 22, the electronic health information data may be processed to adjust certain financial data according to various criteria, such as demographic population. At block 24, a scripting technique, such as a Scala script, Python, R, or another type, may be used to pull the data and process the data for ingestion into future modeling techniques. In one example, the script pulls the tabulated and pre-processed electronic health information data onto an elastic cloud computing system to adjust various metrics, such as financial data and further processing for ingestion into the modeling block 300. The script may use the distributed system of data to process the electronic health information data quickly. This may be necessary due to the many algorithmic and mathematical operations which may be required. The processed electronic health information data may then be stored in elastic SQL for a quality check, as shown at block 26.

Next, within the modeling block 300, the pre-processed electronic health information data from pre-processing block 200 may be input into a stacked regression model at block 28. The stacked regression model may be used to predict future data points relative to the electronic health information data, such as a future financial cost of health care of the patient. Training of the stacked regression model at this stage may also be done, where a scripting language, such as Python, is used to train the weights according to the population of the electronic health information data, the results of which can be stored in pickle format to be used in the prediction of future health costs and risks of the population of the electronic health information data. The weights file may be used to predict the risk and health care costs of patients, where the predicted costs or risks can be stored in the cloud in elastic SQL, such that they can be displayed in a front end data exchange platform, as shown in block 30.

Next, within the output block 400, the predicted costs or risk derived from the processed, modeled, and adjusted electronic health information data may be transmitted to a care coordination facility, such as a facility with the primary objective of managing patient care. This may be a facility which is dedicated to patient management for medical providers within the health care field, or it may be a patient care coordinator within a medical provider. The care coordination facility has a computing system with a dashboard used to manage patients and their representative electronic health information data. The predicted costs or risks may be displayed on the dashboard of the care coordination facility such that representatives may review and prioritize patients based on the predicted costs and risks. Accordingly, the representative of the care coordination facility may review the data and adjust a treatment plan or path for a patient based on the prediction through modeling. This may further include formulating and transmitting automated electronic messages, such as e-mails and SMS messages, and phone calls to patients in order to communicate adjustments to their health care plan. Adjustments to a patient's health care plan may include prioritizing certain patients who have a higher propensity or a higher probability of moving from a low health risk band to a higher risk band, such that these patients can be attended to earlier, and therefore more cost effectively.

While FIG. 2 illustrates various generalized tech stacks which may be used between the various data blocks, it is noted that a variety of specific implements may be employed, depending on the design of the system. For example, the file transfer protocol (FTP) connection may include any file transfer protocol like HTTP, HTTPS, SFTP, Restful API, or others. The scripting language block between data blocks 16 and 18 may include any scripting language, such as SQL, Python, R, C, C++, Scala, and Java, among others. The distributed computing language and framework, such as between data blocks 18 and 20, and 22 and 24 may include any distributed computing language, such as Scala, and framework, such as Spark, among others that may be employed in the art. The database may include various types of databases, such as an ElasticSQL. Other variations to the tech stacks discussed herein may also be employed, all of which are considered within the scope of the present disclosure.

Further details of the method of extraction and conversion of electronic health information data for algorithmic detection of non-linearity to determine treatment path are provided relative to FIGS. 3-7.

Figure 3:
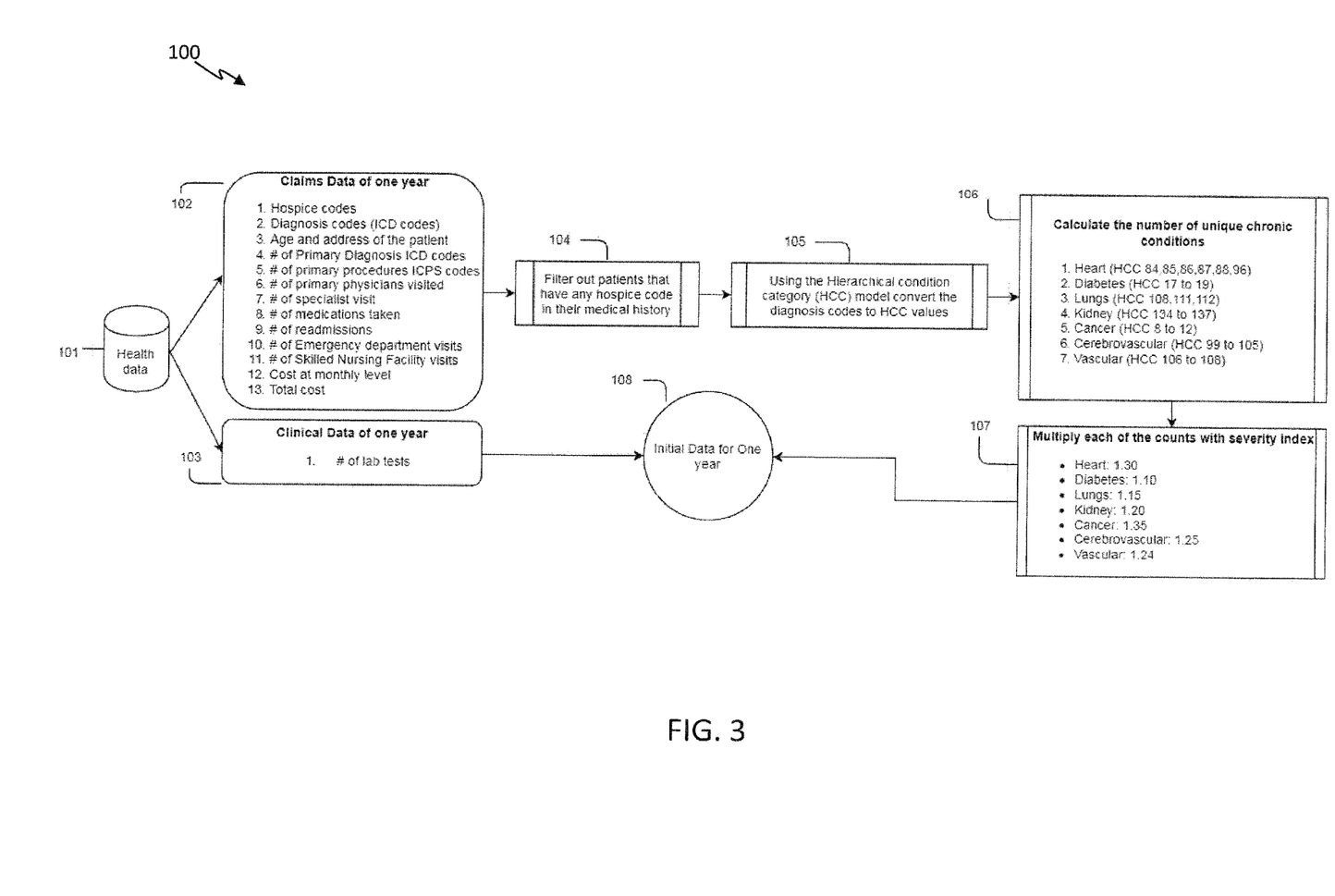
FIG. 3 is a diagrammatical illustration of electronic health information data extraction, in accordance with the first exemplary embodiment of the present disclosure.

FIG. 3 is a diagrammatical illustration of electronic health information data extraction, in accordance with the first exemplary embodiment of the present disclosure. As shown, FIG. 3 illustrates data acquisition and extraction for one predetermined time period of the patient's electronic health information data, such as for one year of data relating to the patient. Similar data acquisition and extraction will follow the same procedure for the second time period, e.g., the second year of the patient's electronic health information records.

The electronic health information database 101 may contain various data points that are to be pulled or extracted from the electronic health information database 101. The electronic health information data that is pulled from the electronic health information database 101 may include claims data 102 for the given time period. This data may include: claims data comprising the disease burden in the form of disease codes like ICD codes, procedure codes, number of primary doctors, or specialist visits; clinical data comprising the lab test codes; medication data; number of readmissions, emergency department visits, skilled nursing facility visits in a year; and the prior costs incurred by the patients on a monthly level. In particular, this data may include:

1 The identity of the hospice status of the patients using the CPT code, HCPCS code, UBREV code & UBTOB code
2 Diagnosis codes of the patients (ICD 9/10 codes)
3 Age and Address of the patient to adjust for the cost of healthcare
4 Number of primary diagnosis codes (ICD codes) in the year
5 Number of primary procedure codes (ICPS codes) in the year
6 Number of primary physicians visited in the year
7 Number of specialist visits in the year
8 Number of unique medications taken in the year
9 Number of 30-day readmissions in the year
10 Number of Emergency Department visits in the year
11 Number of Skilled Nursing Facility Visits in the year
12 Cost breakdown at monthly level
13 Total cost incurred by the patient in the year The clinical data required is depicted at block 103, which namely includes the number of unique lab tests performed during the year for the patient. A filter system 104 is used to remove the patients with hospice codes as they show anomalous behavior in their health cost. Hospice care is a type of care that focuses on the palliation of a chronically ill, terminally ill or seriously ill patient's pain and symptoms, so it is difficult to predict the high cost of such patients.

A mapping technique 105 is used to map the electronic health information data to at least one code model, such as the vast number of Diagnosis codes (ICD-9/10 codes) to its diagnostic condition value, for example, to its Hierarchical Condition Category (HCC) values using the HCC model. The mapping technique may include a counter 106 which counts the unique number of chronic conditions that the patient had in the year using the type of HCC that the patient falls into. The list of chronic conditions may be as follows:

| 1 | Heart | HCC 84,85,86,87,88,96 |
| 2 | Diabetes | HCC 17 to 19 |
| 3 | Lungs | HCC 108,111,112 |
| 4 | Kidney | HCC 134 to 137 |
| 5 | Cancer | HCC 8 to 12 |
| 6 | Cerebrovascular | HCC 99 to 105 |
| 7 | Vascular | HCC 106 to 108 |

As shown at block 107, a severity index is provided which acts to multiply the counts for various chronic conditions counted in block 106. The severity index may include the following severity function multipliers:

| 1 | Heart | 1.30 |
| 2 | Diabetes | 1.10 |
| 3 | Lungs | 1.15 |
| 4 | Kidney | 1.20 |
| 5 | Cancer | 1.35 |
| 6 | Cerebrovascular | 1.25 |
| 7 | Vascular | 1.24 |

The severity index has been calculated based on health information as to which chronic condition is more severe than the other. Interestingly, it must be noted that patients with multiple chronic conditions can be easily detected by the algorithm here leading to a model. Thus the model can understand the correlation between multiple conditions leading to higher costs.

Finally, at block 108, the claims data, demographics data and the clinical data is brought together to form the initial data for the algorithm, which is now ready for the preprocessing, modeling, and other transformations to be performed.

Figure 4:
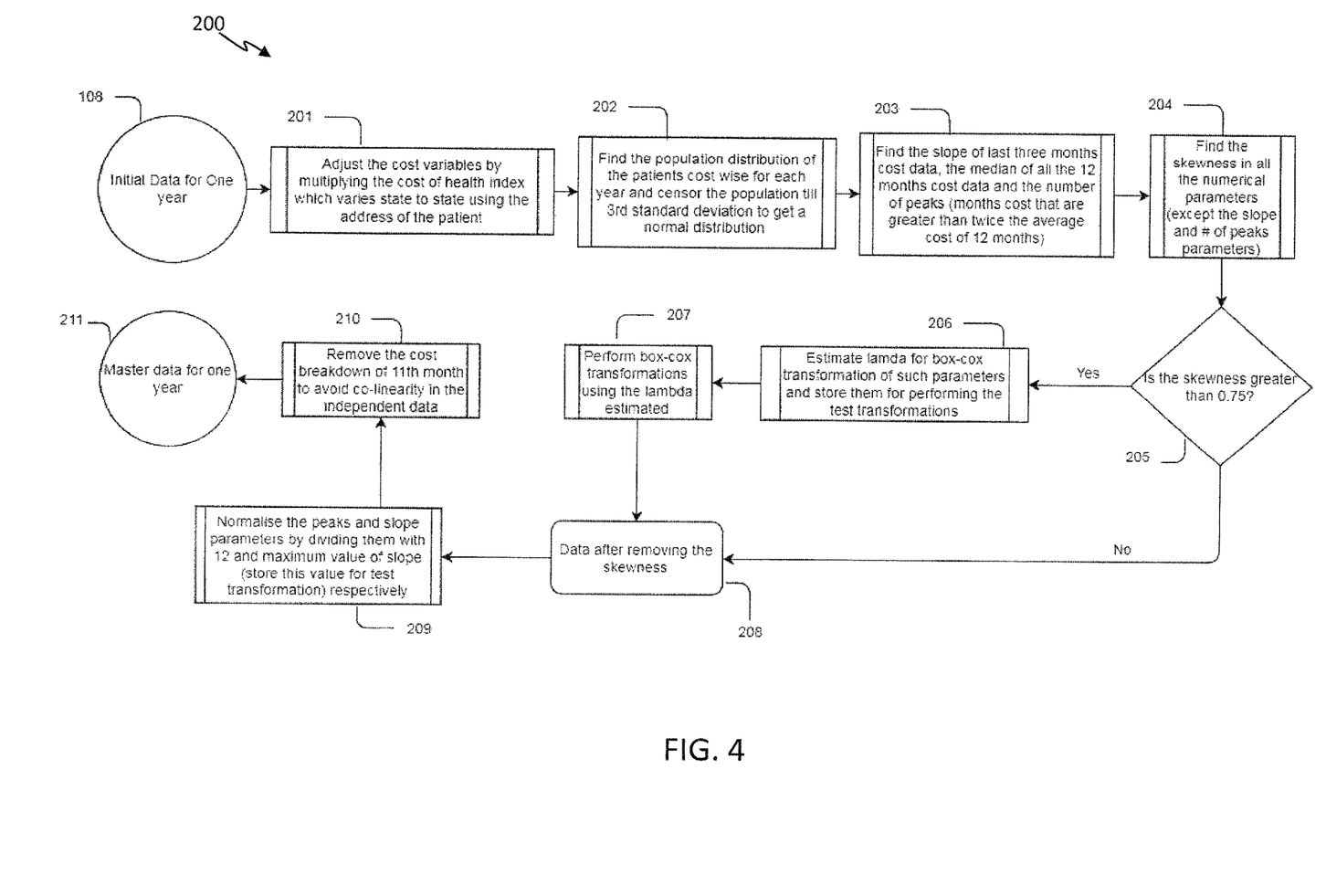
FIG. 4 is a diagrammatical illustration of pre-processing techniques of electronic health information data conversion, in accordance with the first exemplary embodiment of the present disclosure.

FIG. 4 is a diagrammatical illustration of pre-processing techniques of electronic health information data conversion 200, in accordance with the first exemplary embodiment of the present disclosure. As shown, the pre-processing techniques of electronic health information data conversion 200 may include various data transformation and pre-processing techniques which are applied to the initial data set for the given time period (FIG. 3, block 108). The initial data set, e.g., for the first year, is passed through a pre-processing pipeline as described below, and a similar procedure has to be followed for the second year data to pre-process it and make it ready for ingestion into the core modeling engine.

At block 201, an adjustment box adjusts the various cost parameters, such as the total cost and the 12 cost breakdowns, extracted earlier. The adjustment box may use the cost of healthcare index which varies from one jurisdiction to another, such as state-to-state and so forth. In one example, the index can be interpreted as being the inflation or deflation based on where the patient lives, based on the patient's address of record. A censor filter at block 202 is used to determine the population that is supposed to be used for training the model. The censor filter removes the patients who have a total medical cost greater than three times the standard deviation of the population distribution function. This ensures that a Gaussian distribution is achieved to train the model on, as opposed to a right skewed population distribution.

At block 203, a feature extractor is used to build three important features: the slope of the last three months; the number of peaks in the 12 cost breakdowns (monthly costs greater than two times the average cost); and the median cost of the 12 months breakdown. More specifically, the feature extractor may derive the following information for each of the last three time periods (years) for a given individual: maximum cost in 12 months' time frame; average cost for the 12 months; the last two months (M_11+M_12) combined cost; the number of peaks in the cost incurred during the 12 month period (above the 2*average value); the trend in the last three months period i.e. slope of the line with the (M_10, M_11 & M_12) costs with a unit distance on x-axis signifying 1 month period. Any null/NA values in the numerical features may be replaced with 0.

At block 204, a skewness calculator may be used to calculate the skewness in the parameters (other than number of peaks and slope values) to perform homogenizing of the data. During experimentation, it has been found that mostly the cost parameters are skewed that needs transformation. A decision box at block 205 is used to determine whether a box-cox transformation is needed or not based on the condition that skewness should be greater than 0.75. If the condition is true, then a box-cox transformation is required to remove the skewness in the data. As shown at block 206, to perform box-cox transformation on a parameter, a lambda value needs to be estimated. In this case, the Python's stats package boxcox_normmax( ) function can be used. This lambda value is stored in memory for later use when the test set will be evaluated, similar box-cox transformation will be applied using the respective lambda. Box-cox transformation is performed on the data which requires the transformation using the Python stats package boxcox1p( ) function. It is noted that the box-cox transformation method may use the boxcox_normmax function to estimate the optimized lambda for each column and then perform the box-cox transformation on that column.

At block 208, the data is rejoined after removing the skewness in the required features. At block 209, a transformation function may be used to normalize the number of peaks and slopes values by dividing them with 12 and the maximum value in the slope parameter respectively. This maximum value is again stored in memory to be used later during test to convert and normalize the slope values. Next, at block 210, a filter is used to remove the 11th month cost from the breakdown. This is due to the sum of the 12 months cost breakdown being equivalent to the total cost of the year, so to avoid collinearity issue, the filter removes the 11th month cost. Finally, at block 211, the master data is ready for ingestion into the core engine of the algorithm.

Figure 5:
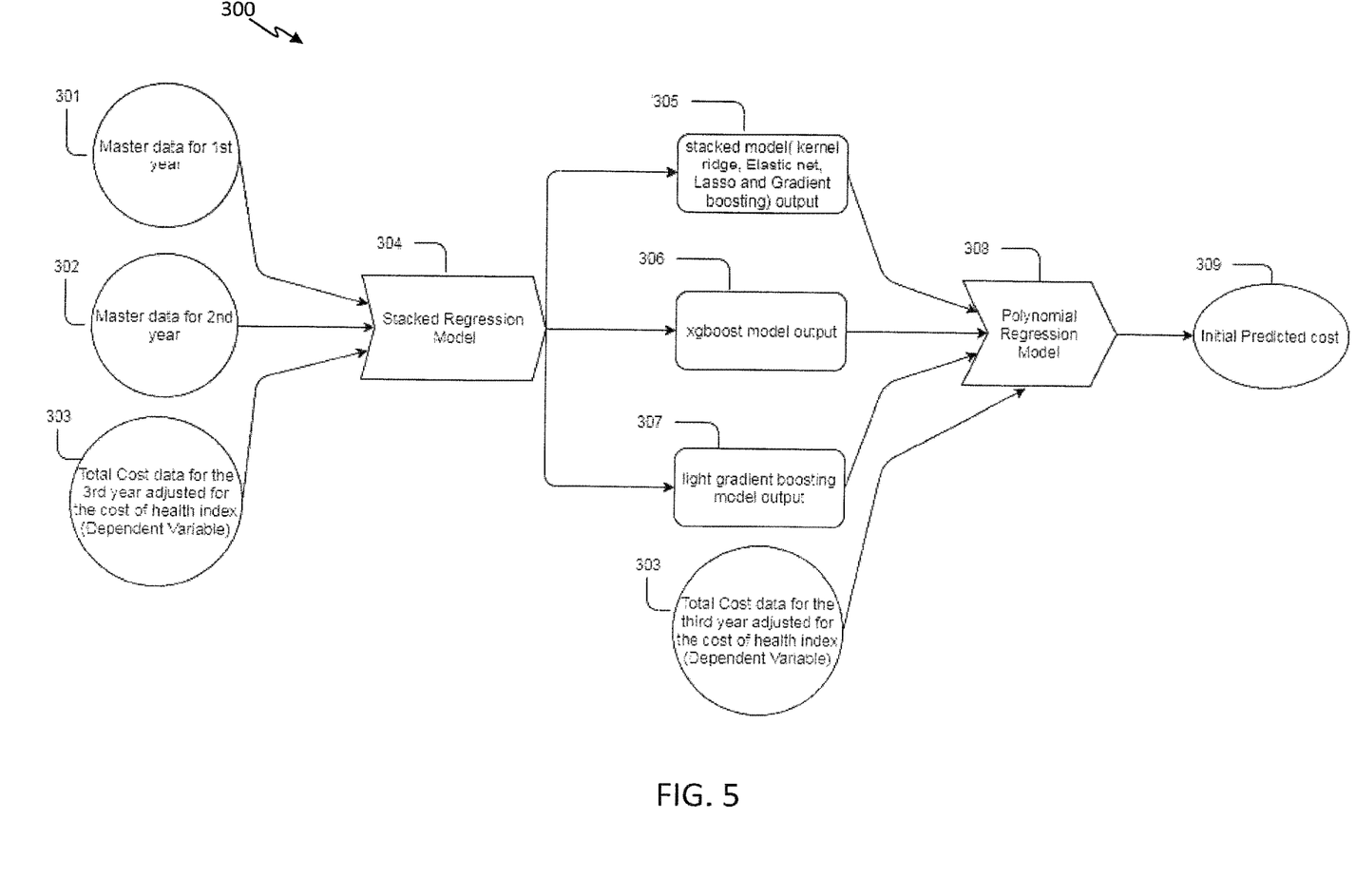
FIG. 5 is a diagrammatical illustration of modeling techniques of electronic health information data using stacked regression models, in accordance with the first exemplary embodiment of the present disclosure.

FIG. 5 is a diagrammatical illustration of modeling techniques of electronic health information data using stacked regression models 300, in accordance with the first exemplary embodiment of the present disclosure. As shown, the modeling techniques of electronic health information data using stacked regression models 300 illustrates the flow of data, both independent data and dependent data, through the model engine, which comprises a stacked regression engine followed by polynomial regression engine. The master data for first year and second year, shown at blocks 301 and 302, respectively, the data of which is achieved through the process detailed relative to FIGS. 4-5, are input as independent variables accompanied with the total cost of third year 303 as the dependent variable. The culmination of the master data for the first and second year, and the third year data is ingested into the model's core engine at block 304.

The model's core engine at block 304 includes the stacked regression model which consists of six basic algorithms namely, Kernel Ridge Regression (KRR), Elastic Net (ENet), Lasso, Gradient Boosting (GBoost), Xtreme Gradient Boosting (xgboost) and Light Gradient Boosting (lgbm). The first four models, i.e., the Kernel Ridge Regression (KRR), Elastic Net (ENet), Lasso, and Gradient Boosting (GBoost) models, are stacked together at block 305 to give an average output using all the models. The other two algorithms i.e., the Xtreme Gradient Boosting (xgboost) and Light Gradient Boosting (lgbm) models, produce two separate outputs called xgboost model output at block 306 and lgbm model output at block 307. A polynomial regression at block 308 of degree 4 is used on the three model outputs as the independent variables and third year cost at block 303 as the dependent variable. The models may produce weights which are stored to be used during testing. The initial prediction at block 309 may be achieved using the polynomial regression of block 308.

In further detail, once the master data is achieved and ready for ingestion into the core model engine, the master data may be split into 80-20 to feed into the model for training. The required features may be selected to be used as independent features in the data and the dependent variables may be separated. During modeling, the stacking average model may be first trained using: base models {ElasticNet, Gradient Boosting, Kernal Ridge regression, Lasso Regression} and meta model {light gradient Boosting model} (stacked_averaged_models=stackingAveragedModels (base_models=(ENet, GBoost, KRR, lasso), meta_model=model_lgb). Next, the model may be trained using the light gradient boosting algorithm, and lastly, the model may be trained using the Extreme Gradient Boosting algorithm.

With regards to class averaging models, it is noted that the models may be given as follows: Base Estimator Model—Elastic net; Regressor Mixing Model—Gradient Boosting; Transformer Mixing Model—Lasso Regressor. Accordingly, each model is made to fit on the data supplied and predict on the test data supplied. The predicted output from all the three models is averaged to give the final output. These models averaged above are stacked upon one another by creating a n_folds number of stacks from the train data. Cloned base models can be trained and to create out-of-fold predictions to use as new features in the meta model. The input is the base models and the meta model to be used in the out-of-fold predictions.

An example of the model configuration (random.seed set to 1000) may be as follows:

```
# LASSO Regression:
lasso = make_pipeline(RobustScaler( ), Lasso (alpha =0.0005,
random_state=1))
# Elastic Net Regression:
ENet = make_pipeline(RobustScaler( ),
ElasticNet(alpha=0.0005, l1_ratio=.9,
random_state=3))
# Kernel Ridge Regression:
KRR = KernelRidge (alpha=0.6, kernel='polynomial', degree=2,
coef0=2.5)
# Gradient Boosting Regression:
GBoost = GradientBoostingRegressor(n_estimators=3000,
learning_rate=0.05,
max_depth=4, max_features='sqrt', min _samples_leaf=15,
min_samples_split=10,
loss='huber', random_state =5)
# XGBoost:
model_xgb = xgb.XGBRegressor(colsample_bytree=0.4603,
gamma=0.0468,
learning_rate=0.05, max_depth=3, n_estimators=2200,
reg_alpha=0.4640,
reg_lambda=0.8571, subsample=0.5213, nthread = -1)
# LightGBM:
model_lgb =
lgb.LGBMRegressor(objective='regression', num_leaves=5,
learning_rate=0.05,
n_estimators=720, max_bin = 55, bagging_fraction = 0.8,
bagging_freq = 5,
feature_fraction = 0.2319, feature_fraction_seed=9,
bagging_seed=9, min_data_in_leaf =6,
min_sum_hessian_in_leaf = 11)
```

The three models are fit using the train data and then test data can be predicted to get the box-cox transformed catp third year value. Once achieved, the box-cox transformed catp third year value can be transformed back to dollar value using the following formula:

$$np.power((y*lambda)+1,(1/lambda))-1)$$

where lambda is the optimized value obtained earlier from boxcox_normmax function during pre-processing steps. Then, ensemble creation may occur, where the three models are used to create an ensemble according to the following formula:

predicted catp third year=0.75*stacked avg. model prediction+0.15*light gradient boosting model prediction+0.15*extreme gradient boosting model prediction From this data, the final predicted value of cost for the next year for each patient can be achieved.

A similar procedure to that described herein should be followed to transform the test data. Specifically, while performing the box-cox transformation the lambda for respective parameters determined from the train data is to be used, similarly to perform the normalization of the slope the maximum value obtained during the training is to be used. There will be two weight files one which contains all the three models (stacked model consisting of ENet, Lasso, KRR & GBoost, xgboost and the lgbm) and the second which has weights for the polynomial regression to fit on. After the initial prediction the differences stored earlier during training are to be added respectively based on where the average adjusted medical cost of the two years falls in the percentile category calculated during training.

Figure 6:
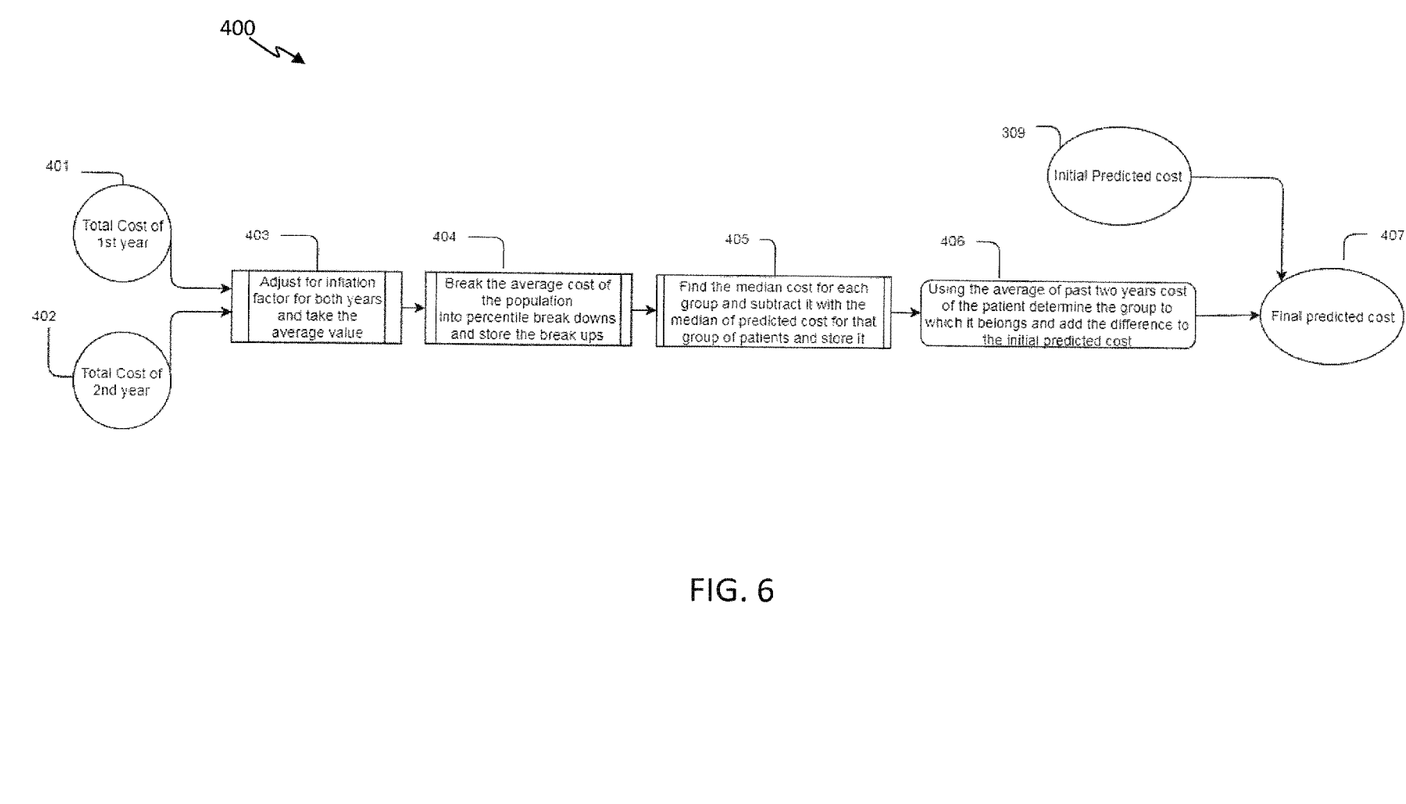
FIG. 6 is a diagrammatical illustration of final adjustments to modeled electronic health information data, in accordance with the first exemplary embodiment of the present disclosure.

FIG. 6 is a diagrammatical illustration of final adjustments to modeled electronic health information data 400, in accordance with the first exemplary embodiment of the present disclosure. In particular, the final adjustments to modeled electronic health information data may be used to derive a final predicted cost of health care for an individual. In the final adjustment, the algorithm takes various factors into account, such as the inflation factor as the time frame of three years during which the training of the model occurs, which may be a significant factor. The inflation adjustment can be skipped in case of concurrent model deployment, but will be needed in prospective scenario. As shown, the total cost for each of the first year and second year, as shown at blocks 401 and 402, is used from the preprocessed database. Each of the total cost for each of the first year and second year is adjusted at block 403 for the inflation factor. Then they are averaged at block 403 and broken down into percentile break-ups at block 404. The percentile breakups percentage may be, in one example: <20%, 20-30%, 30-40%, 40-50%, 50-60%, 60-70%, 70-80%, 80-85%, 85-90%, 90-95%, 95-98%, >98%. The calculated cost according to this percentage breakup is referenced as percentage category. A median cost using this data is calculated at block 405 for each of these groups. Similarly, the median cost of predicted cost for each group is calculated and subtracted from the median calculated earlier, which gives the difference to be added to the initial predicted cost at block 309. Then, upon addition of the initial predicted cost and the difference obtained for each percentile category, the final predicted cost is derived, as shown at block 407. If, upon addition of the difference, the value becomes negative, then the initial predicted value may be kept as the final predicted value.

Figure 7:
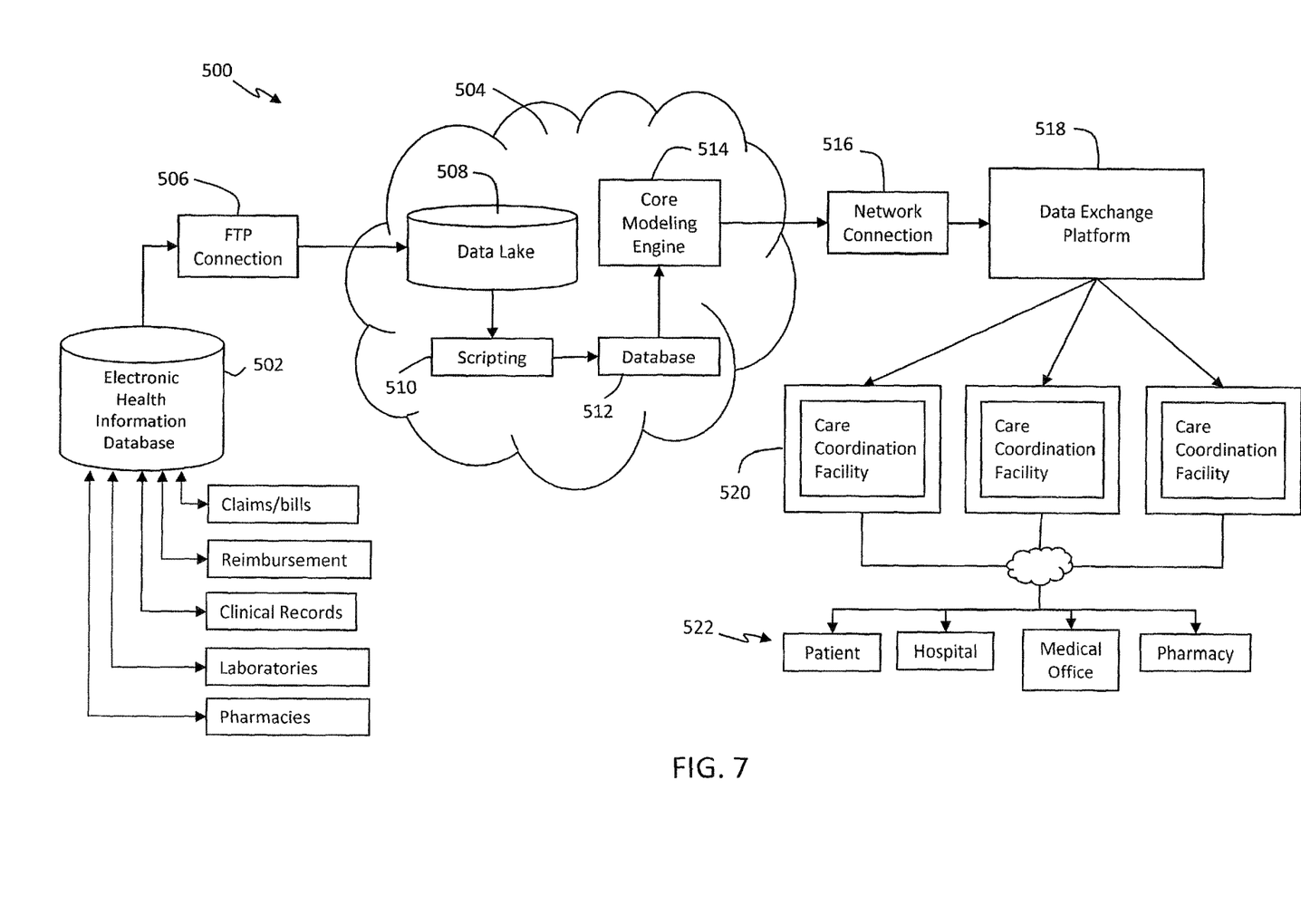
FIG. 7 is diagrammatical illustration of the architecture of a system of extraction and conversion of electronic health information data for training a computerized data model for algorithmic detection of non-linearity in a data set, in accordance with the first exemplary embodiment of the present disclosure.

FIG. 7 is diagrammatical illustration of the architecture of a system of extraction and conversion of electronic health information data for training a computerized data model for algorithmic detection of non-linearity in a data set 500, in accordance with the first exemplary embodiment of the present disclosure. The system of extraction and conversion of electronic health information data for training a computerized data model for algorithmic detection of non-linearity in a data set 500, which may be referred to herein as system 500, may include the electronic health information database 502 which is connected through a network connection with a cloud computing device 504. The electronic health information database 502 may receive a variety of electronic health information data from a variety of sources, including claims and/or billing providers, entities for the reimbursement of payers, clinical records databases, independent laboratories, pharmacies, health care providers, and others. The network connection may be a FTP connection 506, as shown, which may be used to pull the electronic health information data from the electronic health information database 502 to the data lake 508. The pre-processing, processing, and modeling components may be housed on and/or operated from the cloud computing device, including the scripting block 510, the database 512, and the core modeling engine 514.

After the electronic health information data is processed through these processing and modeling techniques, it is transmitted through a network 516 to a data exchange platform 518 as the final predicted value or a predictive data set which can be used to predict a cost increase in a patient's health care. The predictive data set may also include a prioritization assessment of at least one patient which provides data or a recommendation for adjustment of the patient's health care regimen such that they can be prioritized in order to best accommodate for predicated changes in their health.

The data exchange platform 518 may be hosted independently of the cloud computing device 504. The data exchange platform 518 may have a dashboard for viewing, analyzing, and manipulating the predictive data set as needed. In communication with data exchange platform 518 are a variety of care coordination facilities 520, which are commonly health care organizations or entities who oversee, advise on, or control the health care plan or path of an individual patient or a collective group of patients. Each of the care coordination facilities 520 includes a computing system which is configured to receive data transmission from the data exchange platform 518, and each of the computing systems of the care coordination facilities 520 has a dashboard or user interface which lists health related data of patients.

The feed from the data exchange platform 518 into the computing system of the care coordination facilities 520 may automatically update, adjust, advise, or alert a representative of the care coordination facilities 520 about a particular health care issue with a patient based on the predictive data set or the prioritization assessment of the patient. For example, if the predictive data set for Patient A has shown that the patient is likely to be susceptible for a particular health condition, the file for Patient A on the computing system of the care coordination facility 520 may be updated with the predictive data set. In this case, the care coordination facility 520 may contact Patient A or a health care provider for Patient A to adjust his or her health care path or plan. For example, the dashboard of the computing system of the care coordination facility 520 may automatically transmit a message to Patient A or their health care provider, such as a medical office, pharmacy, or hospital, to schedule an appointment or to adjust a medical regimen. The transmission of the message may include electronic messages such as e-mails or SMS messages, but it may also include automated phone calls, paper letters, alerts or other indicators to inform Patient A or a health care provider of Patient A of the change in their regimen.

Figure 8:
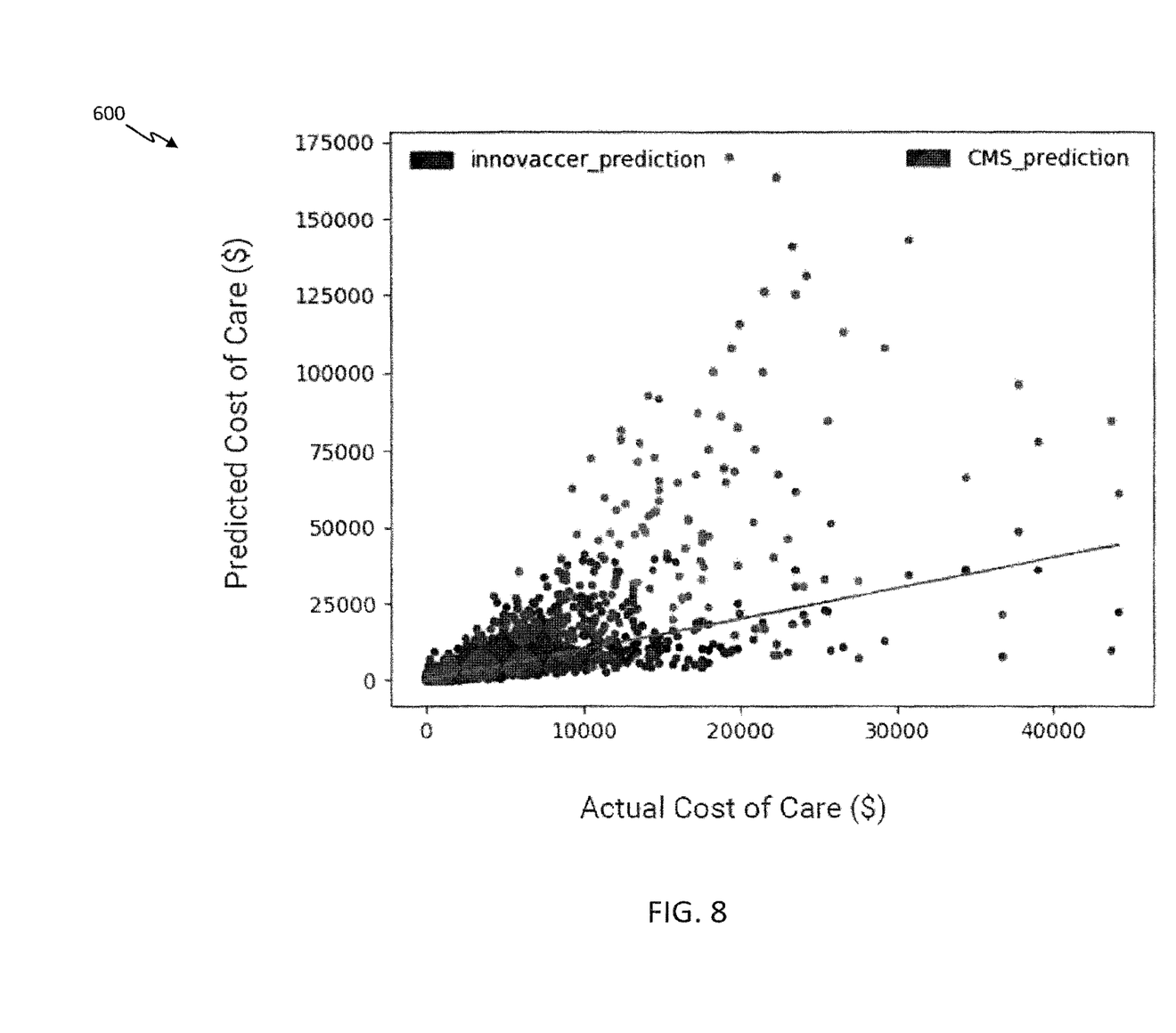
FIG. 8 is graphical illustration of a comparison of data prediction results and actual results between conventional methods and the computerized data model for algorithmic detection of non-linearity in a data set, in accordance with the first exemplary embodiment of the present disclosure.

FIG. 8 is graphical illustration 600 of a comparison of data prediction results to actual results between conventional methods and the computerized data model for algorithmic detection of non-linearity in a data set, in accordance with the first exemplary embodiment of the present disclosure. In particular the graphical illustration 600 depicts the accuracy of a prediction of health costs as compared to actual health costs for both conventional models, such as those used by governmental agencies, and those described in the current disclosure. One such governmental agency that aims to predict health costs is the Center for Medicare and Medicaid Service (CMS). CMS conventionally uses a HCC risk model which may be accurate for population level benchmarking of cost. However, it has been found to be far less accurate for predicting costs on an individual patient level. In contrast, the model described herein accounts for the non-linearity of the actual data in making predictions, and it relies on additional aspects, such as disease interactions and the progression of chronic conditions, and interactions therebetween, which results in a far more accurate prediction on the individual patient level than conventionally seen with the CMS model or other models.

Turning to the graphical illustration 600, the predictions may be made relative to a linear model using regression analysis where the R-squared ($R^2$) value provides an assessment for the coefficient of determination, or closeness of fit of the data to the model. As can be seen, the data points for different patients are graphed relative to the linear model and the data points corresponding to the CMS prediction are less accurate than the data points corresponding to the subject system and method disclosed herein. In particular, the R-squared value of the subject system and method is 0.54 whereas the R-squared value of the CMS prediction is 0.12, which equates to the methodology of the subject disclosure being approximately five times greater in accuracy of predicting the total cost of care for patients than the conventional model. Accordingly, this better prediction can be used to provide significantly better planning, care, and cost management for patients, healthcare providers, and healthcare payers.

It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A method for training a computerized data model for the algorithmic detection of non-linearity in an electronic health information data set, the method comprising:
   providing at least two master data sets corresponding to two discrete time periods, respectively, and a third data set for a third discrete time period, wherein the two master data sets are mapped to at least one code model by at least one of:
      converting a quantity of electronic health information data in unstructured format to tabular format for storage on a distributed file system (DFS);
      semantic unification of the quantity of electronic health information data; and
      mapping at least one diagnostic code within the quantity of electronic health information data to a hierarchical condition category (HCC) value using a HCC model, summing a plurality of HCC values, and processing the summed plurality of HCC values through a severity index;
   training a stacking average model with the at least two master data sets corresponding to two discrete time periods by:
      using a first model comprising: a Kernel Ridge Regression (KRR) algorithm, an Elastic Net (ENet) algorithm, a Least Absolute Shrinkage and Selection Operator (Lasso) algorithm, and a Gradient algorithm stacked together;

using a second model comprising a Light Gradient Boosting (lgbm) algorithm; and using a third model comprising an Xtreme Gradient Boosting (xgboost) algorithm;

applying a box-cox transformation function to the first, second, and third models of the stacking average model to provide a predicted value for the third data set of the third discrete time period; and creating an ensemble to identify a non-linearity in the third data set, the ensemble using the predicted value for the third data set as a function of the first, second, and third models of the trained stacking average model, wherein the first model is weighted by 0.75, the second model is weighted by 0.15, and the third model is weighted by 0.15.

2. A method for extraction and conversion of electronic health information data for algorithmic detection of non-linearity to determine treatment path, the method comprising the steps of:

extracting, via a file transfer connection, a quantity of electronic health information data from a health database to a data lake on a computerized cloud server;

mapping at least a portion of the quantity of electronic health information data to at least one code model to produce an initial data set;

scripting the initial data set for pre-processing to determine a skewness of the initial data set and removing skewness of the initial data set to provide a master data set associated with at least two discrete time periods, wherein when the determined skewness is greater than 0.75, skewness of the initial data set is removed with a boxcox1p( ) function box-cox transformation, and when the determined skewness is less than 0.75, skewness of the initial data set is removed without the boxcox1p( ) function box-cox transformation;

modeling the master data set for the at least two discrete time periods with a stacked regression model and a polynomial regression model to produce a predictive data set, wherein the master data set for one time period of the two discrete time periods is an independent variable and the master data set for another time period of the two discrete time periods is a dependent variable, wherein the predictive data set is expressed as a boxcox1p( ) function box-cox transformed value of a third discrete time period;

converting the boxcox1p( ) function box-cox transformed value of the third discrete time period to a predictive monetary value using an inverse boxcox1p( ) function box-cox transformation;

transmitting the predictive monetary value to a data exchange platform, wherein the predictive monetary value provides a prioritization assessment of patients associated with the quantity of electronic health information data; and implementing the prioritization assessment in a care coordination facility to determine a treatment path of the patients, whereby the treatment path of at least one patient is adjusted.

3. The method of claim 2, wherein the stacked regression model further comprises: a Kernel Ridge Regression (KRR) algorithm, an Elastic Net (ENet) algorithm, a Lasso algorithm, a Gradient algorithm, an Xtreme Gradient Boosting (xgboost) algorithm, and a Light Gradient Boosting (lgbm) algorithm.

4. The method of claim 3, wherein the Kernel Ridge Regression (KRR) algorithm, the Elastic Net (ENet) algorithm, the Lasso algorithm, and the Gradient algorithm are stacked together.

5. The method of claim 4, wherein the polynomial regression model receives inputs consisting of: the stacked Kernel Ridge Regression (KRR) algorithm, Elastic Net (ENet) algorithm, Lasso algorithm, and Gradient algorithm; the Xtreme Gradient Boosting (xgboost) algorithm; the Light Gradient Boosting (lgbm) algorithm; and data associated with at least the third discrete time period.

6. The method of claim 2, wherein mapping the quantity of electronic health information data to the at least one code model to produce the initial data further comprises at least one of:

converting the quantity of electronic health information data in unstructured format to tabular format for storage;

semantic unification of the quantity of electronic health information data; and mapping at least one diagnostic code to a diagnostic condition value using a model and summing a plurality of code values and processing the summed plurality of code values through a severity index.

7. The method of claim 6, wherein, mapping the at least one diagnostic code to a diagnostic condition value further comprises mapping the at least one diagnostic code to a hierarchal condition category (HCC) value using a HCC model and summing a plurality of HCC values and processing the summed plurality of HCC values through the severity index.

8. The method of claim 2, wherein scripting the initial data set for preprocessing further comprises executing a censor filter, a feature extractor, and a skewness calculator.

9. The method of claim 2, wherein when the skewness of the initial data set is removed with the boxcox1p( ) function box-cox transformation, a transformation function is applied which normalizes peaks and slope values of the initial data set.

10. The method of claim 2, wherein implementing the prioritization assessment in the care coordination facility further comprises transmitting the prioritization assessment through at least one network connection to a computing system of the care coordination facility, whereby a dashboard of the computing system displays the prioritization assessment for the at least one patient.

11. The method of claim 10, further comprising automatically communicating with a medical care facility from the computing system of the care coordination facility to adjust a treatment path of the at least one patient.

12. The method of claim 11, wherein automatically communicating with the medical care facility further comprises transmitting at least one of: a phone call, an electronic message, and a non-electronic data message to the at least one patient.

13. A system for computerized extraction and conversion of electronic health information data using a computerized cloud server having at least a processor and a memory for algorithmic detection of non-linearity to determine treatment path, the system comprising:

a quantity of electronic health information data on a health database, wherein at least a portion of the quantity of electronic health information data is extracted via a file transfer connection to a data lake on the computerized cloud server;

at least one code model to produce an initial data set, wherein the initial data set is produced by mapping at least a portion of the quantity of electronic health information data to the at least one code model;

a script for scripting the initial data set for preprocessing to determine a skewness of the initial data set and to remove the skewness of the initial data set to provide a master data set associated with at least two discrete time periods, wherein when the determined skewness is greater than 0.75, skewness of the initial data set is removed with a boxcox1p( ) function box-cox transformation, and when the determined skewness is less than 0.75, skewness of the initial data set is removed without the boxcox1p( ) function box-cox transformation;

a modeling engine to model the master data set for the at least two discrete time periods with a stacked regression model and a polynomial regression model to produce a predictive data set for a third discrete time period, wherein the master data set for one time period of the two discrete time periods is an independent variable and the master data set for another time period of the two discrete time periods is a dependent variable, wherein the predictive data set is expressed as a boxcox1p( ) function box-cox transformed value of the third discrete time period, and wherein the boxcox1p( ) function box-cox transformed value of the third discrete time period is converted to a predictive monetary value using an inverse boxcox1p( ) function box-cox transformation;

a data exchange platform, wherein the predictive monetary value is transmitted to the data exchange platform, wherein the predictive monetary value provides a prioritization assessment of patients associated with the quantity of electronic health information data; and a care coordination facility to which the prioritization assessment is transmitted and in which the prioritization is implemented to determine a treatment path of the patients, whereby the treatment path of at least one patient is adjusted.

14. The system of claim 13, wherein the stacked regression model further comprises: a Kernel Ridge Regression (KRR) algorithm, an Elastic Net (ENet) algorithm, a Least Absolute Shrinkage and Selection Operator (Lasso) algorithm, a Gradient algorithm, an Xtreme Gradient Boosting (xgboost) algorithm, and a Light Gradient Boosting (lgbm) algorithm.

15. The system of claim 14, wherein the Kernel Ridge Regression (KRR) algorithm, the Elastic Net (ENet) algorithm, the Lasso algorithm, and the Gradient algorithm are stacked together.

16. The system of claim 13, wherein mapping the quantity of electronic health information data to the at least one code model to produce the initial data further comprises at least one of:

converting the quantity of electronic health information data in unstructured format to tabular format for storage;

semantic unification of the quantity of electronic health information data; and mapping at least one diagnostic code to a diagnostic condition value using a model and summing a plurality of code values and processing the summed plurality of code values through a severity index.

17. The system of claim 13, wherein mapping the at least one diagnostic code to a diagnostic condition value further comprises mapping the at least one diagnostic code to a hierarchical condition category (HCC) value using a HCC model and summing a plurality of HCC values and processing the summed plurality of HCC values through a severity index.

18. The system of claim 13, wherein scripting the initial data set for pre-processing further comprises executing a censor filter, a feature extractor, and a skewness calculator.

19. The system of claim 13, wherein when the skewness of the initial data set is removed with the boxcox1p( ) function box-cox transformation, a transformation function is applied which normalizes peaks and slope values of the initial data set.

20. The system of claim 13, wherein implementing the prioritization assessment in the care coordination facility further comprises transmitting the prioritization assessment through at least one network connection to a computing system of the care coordination facility, whereby a dashboard of the computing system displays the prioritization assessment for the at least one patient.

21. The system of claim 20, further comprising automatically communicating with a medical care facility from the computing system of the care coordination facility to adjust a treatment path of the at least one patient.

22. The system of claim 21, wherein automatically communicating with the medical care facility further comprises transmitting at least one of: a phone call, an electronic message, and a non-electronic data message to the at least one patient.

* * * * *

UNITED STATES PATENT AND TRADEMARK OFFICE
CERTIFICATE OF CORRECTION

PATENT NO. : 10,789,266 B2
APPLICATION NO. : 16/363897
DATED : September 29, 2020
INVENTOR(S) : Bhabesh et al.

Page 1 of 1

It is certified that error appears in the above-identified patent and that said Letters Patent is hereby corrected as shown below:

On the Title Page

At Item (54) and in the Specification at Column 1, Lines 1-6:
"SYSTEM AND METHOD FOR EXTRACTION AND CONVERSION OF ELECTRONIC HEALTH INFORMATION FOR TRAINING A COMPUTERIZED DATA MODEL FOR ALGORITHMIC DETECTION OF NON-LINEARITY IN A DATA"
Should be:
--SYSTEM AND METHOD FOR EXTRACTION AND CONVERSION OF ELECTRONIC HEALTH INFORMATION FOR TRAINING A COMPUTERIZED DATA MODEL FOR ALGORITHMIC DETECTION OF NON-LINEARITY IN A DATA SET--

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*